US009170207B2

(12) United States Patent
Perriollat

(10) Patent No.: US 9,170,207 B2
(45) Date of Patent: Oct. 27, 2015

(54) 3D INSPECTION USING CAMERAS AND PROJECTORS WITH MULTIPLE-LINE PATTERNS

(75) Inventor: Mathieu Perriollat, Fontaine (FR)

(73) Assignee: VIT, Saint Egreve (FR)

( * ) Notice: Subject to any disclaimer, the term of this patent is extended or adjusted under 35 U.S.C. 154(b) by 272 days.

(21) Appl. No.: 13/190,195

(22) Filed: Jul. 25, 2011

(65) Prior Publication Data

US 2012/0019651 A1  Jan. 26, 2012

(30) Foreign Application Priority Data

Jul. 26, 2010  (FR) ..................................... 10 56086

(51) Int. Cl.
*H04N 7/18* (2006.01)
*G01N 21/88* (2006.01)
*G01B 11/25* (2006.01)
*G01N 21/956* (2006.01)
*G06T 1/00* (2006.01)
*G01R 31/308* (2006.01)

(52) U.S. Cl.
CPC ........ *G01N 21/8851* (2013.01); *G01B 11/2545* (2013.01); *G01N 21/956* (2013.01); *G06T 1/0007* (2013.01); *G01N 2201/0635* (2013.01); *G01R 31/308* (2013.01)

(58) Field of Classification Search
CPC . H04N 7/18; G01B 11/2545; G01N 21/8851; G01N 2201/0635; G01N 21/956; G06T 1/0007; G01R 31/308; H01N 21/8851
USPC .................... 348/87, 92; 340/935; 356/239.1; 382/154
See application file for complete search history.

(56) References Cited

U.S. PATENT DOCUMENTS

| 5,276,613 | A  | * | 1/1994 | Schlumberger ................... 378/4 |
| 5,331,174 | A  | * | 7/1994 | Dassler et al. ........... 250/559.24 |
| 5,442,444 | A  | * | 8/1995 | Landwehr ...................... 356/604 |
| 6,519,497 | B1 | * | 2/2003 | Blome et al. .................... 700/58 |
| 6,542,249 | B1 | * | 4/2003 | Kofman et al. ................ 356/601 |
| 6,717,625 | B1 | * | 4/2004 | Thielemans .................. 348/745 |
| 6,795,200 | B1 | * | 9/2004 | Barman et al. ................ 356/606 |
| 2002/0027608 | A1 | * | 3/2002 | Johnson et al. ............... 348/383 |

(Continued)

FOREIGN PATENT DOCUMENTS

| DE | 4301546 A1 | 7/1994 |
| EP | 0867689 A2 | 9/1998 |

(Continued)

OTHER PUBLICATIONS

Search Report issued in French Application No. 1056086 on Apr. 11, 2011.

*Primary Examiner* — Jay Patel
*Assistant Examiner* — Joseph Suh
(74) *Attorney, Agent, or Firm* — Vedder Price, P.C.

(57) ABSTRACT

An installation of optical inspection of integrated circuits or the like includes a photographic system placed above a scene in a plane defined by a first and a second direction, the photographic system having several digital cameras each having an orthogonal array of pixels, all cameras having their respective optical axes inclined by a first angle with respect to a third direction perpendicular to the two others; and two projectors of determined patterns, these patterns being such that two straight lines projected by each of the projectors are aligned in the plane defined by the first two directions and are coplanar with a straight line interconnecting the optical centers of the two projectors.

8 Claims, 4 Drawing Sheets

(56) References Cited

U.S. PATENT DOCUMENTS

| | | | |
|---|---|---|---|
| 2002/0029125 A1* | 3/2002 | Pratt et al. | 702/127 |
| 2002/0061131 A1* | 5/2002 | Sawhney et al. | 382/154 |
| 2002/0177885 A1* | 11/2002 | Eisfeld et al. | 607/89 |
| 2002/0196432 A1* | 12/2002 | Ishiura et al. | 356/237.1 |
| 2003/0164953 A1* | 9/2003 | Bauch et al. | 356/611 |
| 2003/0184767 A1* | 10/2003 | Tu et al. | 356/614 |
| 2003/0218761 A1* | 11/2003 | Tomasi et al. | 356/627 |
| 2004/0052501 A1* | 3/2004 | Tam | 386/46 |
| 2004/0076739 A1* | 4/2004 | Yokono et al. | 427/8 |
| 2004/0117638 A1* | 6/2004 | Monroe | 713/186 |
| 2004/0246473 A1* | 12/2004 | Hermary et al. | 356/237.1 |
| 2005/0219375 A1* | 10/2005 | Hasegawa et al. | 348/211.2 |
| 2006/0038978 A1* | 2/2006 | Zweig et al. | 356/56 |
| 2006/0103724 A1* | 5/2006 | Jongsma et al. | 348/78 |
| 2006/0228018 A1* | 10/2006 | Abramovich et al. | 382/141 |
| 2006/0244959 A1* | 11/2006 | Yagita | 356/239.6 |
| 2006/0268264 A1* | 11/2006 | Ackley et al. | 356/237.1 |
| 2007/0120977 A1* | 5/2007 | Duquette et al. | 348/87 |
| 2008/0278718 A1* | 11/2008 | Sonda | 356/239.8 |
| 2009/0022410 A1* | 1/2009 | Haskell | 382/238 |
| 2009/0080706 A1* | 3/2009 | Tao et al. | 382/110 |
| 2009/0213366 A1* | 8/2009 | Nakano et al. | 356/239.1 |
| 2009/0274361 A1* | 11/2009 | Schwab et al. | 382/145 |
| 2009/0294420 A1* | 12/2009 | Abramov et al. | 219/121.69 |
| 2010/0065757 A1* | 3/2010 | Schwab et al. | 250/491.1 |
| 2010/0091272 A1* | 4/2010 | Asada et al. | 356/237.2 |
| 2010/0092040 A1* | 4/2010 | Fischer | 382/106 |
| 2010/0118138 A1* | 5/2010 | Djachiachvili | 348/125 |
| 2010/0309308 A1* | 12/2010 | Saphier et al. | 348/92 |
| 2011/0050889 A1* | 3/2011 | Kiuchi et al. | 348/135 |
| 2011/0069154 A1* | 3/2011 | Case et al. | 348/46 |
| 2011/0080306 A1* | 4/2011 | Leopold et al. | 340/935 |
| 2011/0234920 A1* | 9/2011 | Nelson | 348/745 |
| 2013/0020392 A1* | 1/2013 | Olmstead et al. | 235/440 |

FOREIGN PATENT DOCUMENTS

| | | |
|---|---|---|
| EP | 1746816 A1 | 1/2007 |
| WO | 2009090633 A2 | 7/2009 |

* cited by examiner

3D INSPECTION USING CAMERAS AND PROJECTORS WITH MULTIPLE-LINE PATTERNS

CROSS REFERENCE TO RELATED APPLICATIONS

The instant disclosure is related to a co-pending application filed under Ser. No. 13/190,149 on Jul. 25, 2011.

BACKGROUND OF THE INVENTION

1. Field of the Invention

The present invention generally relates to optical inspection systems and, more specifically, to systems for the in-line analysis of electronic circuits. The present invention more specifically relates to systems equipped with digital cameras.

2. Discussion of Prior Art

FIG. 1 schematically shows an installation of the type to which the present invention applies as an example. Electronic circuits IC, for example supported by a printed circuit board ICC, are placed, for example, on a conveyor of an in-line optical inspection installation. Such an installation comprises a system 2 of digital cameras, connected to an image processing computer system 3. Conveyor 1 is capable of moving in a plane X, Y (generally horizontal) and, for a series of photographs, in one of the two directions only, that is, direction X.

To decrease processing costs, it is generally desired to compensate for a limited quality of the images by a digital processing of these images. In particular, it has already been provided to compensate for a low camera resolution by taking several images, slightly offset with respect to one another in both directions of the plane and by implementing a so-called super-resolution technique.

For example, document WO2009/090633 describes an inspection installation using an array network of several digital cameras which is displaced with respect to the photographed object to implement a super-resolution technique. To increase the image resolution in both directions of the plane by means of such a system, a camera network must be used and displaced, either in both directions of the plane, or in an oblique direction with respect to the conveying direction. This complicates the system mechanism and increases its cost due to the accuracy required for the drive motors.

Another object of some optical inspection systems is to obtain three-dimensional images. An installation such as described in the above-mentioned document is not adapted to the reconstruction of three-dimensional images.

It would be desirable to have an installation for analyzing objects of integrated circuit type by image processing, which allows the use of a lesser number of cameras than conventional system, with no loss of resolution.

It would also be desirable to have an installation adapted to three-dimensional analysis.

It would also be desirable to have a system of low cost as compared with known solutions.

SUMMARY OF THE INVENTION

An object of an embodiment of the present invention is to provide an installation of inspection by image analysis which overcomes all or part of the disadvantages of known methods and installations.

According to a first aspect, an object of an embodiment of the present invention is to provide a solution which is particularly well adapted to an in-line processing and which simplifies displacements.

According to this first aspect, another object of another embodiment of the present invention is to provide a particularly simple solution for a two-dimensional analysis.

According to a second aspect, an object of an embodiment of the present invention is to provide a solution adapted to the obtaining of three-dimensional images.

Another object of an embodiment is to provide a solution compatible with the two aspects.

To achieve all or part of these and other objects, the present invention provides an installation of optical inspection of integrated circuits or the like, comprising:

a photographic system placed above a scene in a plane defined by a first and a second direction, the photographic system comprising several digital cameras each comprising an orthogonal array of pixels, all cameras having their respective optical axes inclined by a first angle with respect to a third direction perpendicular to the two others; and two projectors of determined patterns, these patterns being such that two straight lines projected by each of the projectors are aligned in the plane defined by the first two directions and are coplanar with a straight line interconnecting the optical centers of the two projectors.

According to an embodiment of the present invention, the first angle ranges between 15 and 25 degrees.

According to an embodiment of the present invention, four cameras are associated with each projector and are oriented to aim at a same point on the viewing axis of this projector.

According to an embodiment of the present invention, said patterns are such that two straight lines projected by each of the projectors are aligned in a plane defined by the first two directions and are coplanar with a straight line interconnecting the optical centers of the two projectors.

According to an embodiment of the present invention, an image processing system is capable of applying a super-resolution processing to a succession of images provided by the photographic system.

According to an embodiment of the present invention, the installation further comprises a conveyor of the objects to be analyzed in a first direction of said plane, the photographic system being placed above an area of the conveyor and in a fixed position with respect thereto and said cameras being distributed in two sets of cameras aligned in a second direction different from the first one, the cameras being all oriented so that one of the orthogonal directions of their pixel array forms a second angle ($\alpha$) with the first direction.

According to an embodiment of the present invention, the second direction is perpendicular to the first one.

According to an embodiment of the present invention, the pixels of the different cameras are aligned with the second direction.

According to an embodiment of the present invention, the second angle ranges between 3 and 20 degrees.

The present invention also provides a method for controlling such an optical inspection installation.

The foregoing and other objects, features, and advantages of the present invention will be discussed in detail in the following non-limiting description of specific embodiments in connection with the accompanying drawings.

DETAILED DESCRIPTION

Figure 1:
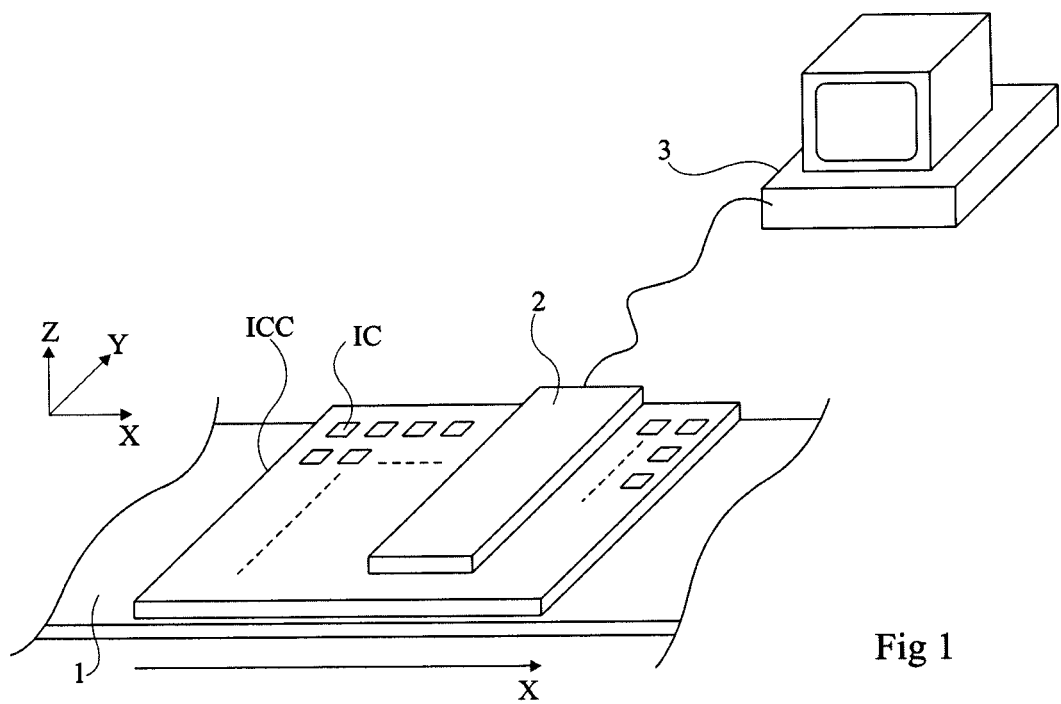
FIG. 1, previously described, very schematically shows an example of an integrated circuit inspection installation of the type to which the present invention applies.

The same elements have been designated with the same reference numerals in the different drawings, which have been drawn out of scale. For clarity, only those steps and elements which are useful to the understanding of the present invention have been shown and will be described. In particular, the image processing algorithms used by the present invention are known per se and will not be detailed. Further, the practical implementation of a digital image sensor has not been detailed, the present invention being compatible with any usual black and white or color array camera, for example, charge-coupled devices (CCD) or CMOS sensors.

The present invention will first be described in relation with its first aspect, applied to an embodiment for a two-dimensional photography installation.

Figure 2:
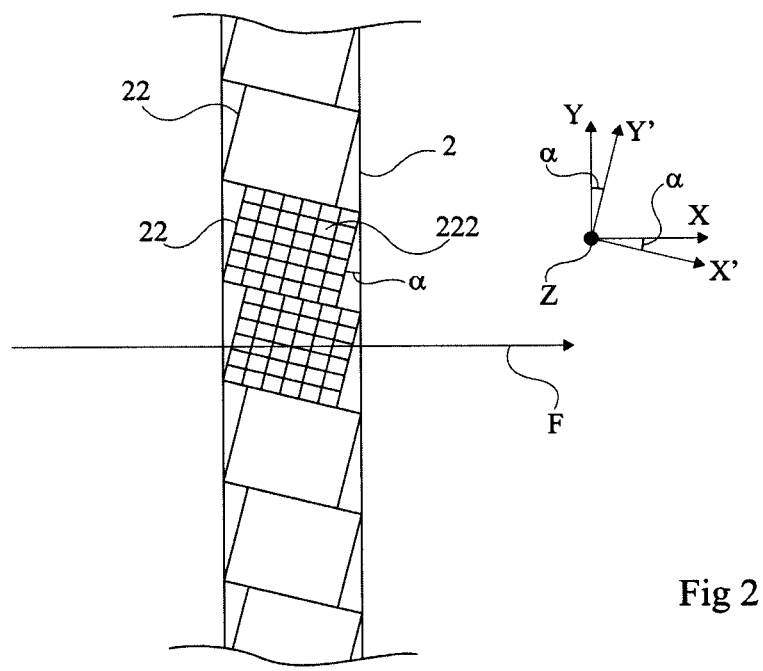
FIG. 2 is a simplified representation of digital sensors according to an embodiment of the first aspect of the present invention.

FIG. 2 is a simplified top view showing a set 2 of image sensors 22 of an analysis installation according to an embodiment of the first aspect of the present invention. It is provided to displace the objects to be photographed (for example, the integrated circuits of FIG. 1) with respect to the sensor system, and for the sensors to be fixed. For a two-dimensional photography installation, sensors 22 are all coplanar in a plane parallel to the plane (X, Y) of the circuit conveyor.

In the embodiment of FIG. 2, the images sensors are placed so that their respective pixels 222 form an array along perpendicular directions, which are not aligned with axes X and Y. This amounts to rotating each sensor by a same angle $\alpha$ around vertical axis Z, so that the pixels are aligned along directions parallel to axes X', Y' defining a reference frame which forms an angle $\alpha$ with respect to reference frame X, Y. Here, sensors 22 are however aligned along direction Y, that is, perpendicularly to conveying direction X. On displacement of an object under camera system 2 along direction F parallel to axis X, a point of the object passes from one pixel to another in both sensor directions, that is, at different positions in the pixel.

Figure 2A:
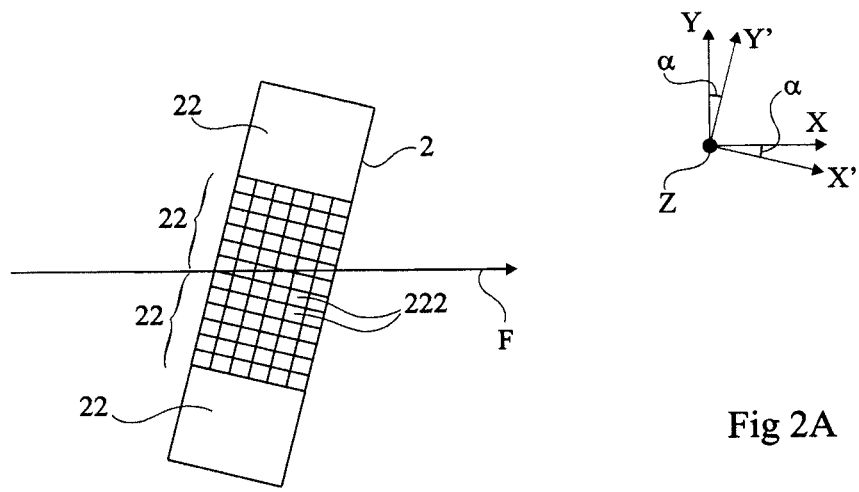
FIG. 2A is a simplified representation of digital sensors according to another embodiment of the first aspect of the present invention.

FIG. 2A illustrates a variation according to which sensors 22 are aligned with axis Y'. The row of sensors is then aligned with respect to axis Y by an angle $\alpha$. As compared with the embodiment of FIG. 5, an advantage is that a setting of angle $\alpha$ is simpler since it is performed only once on all sensors.

Figure 3:
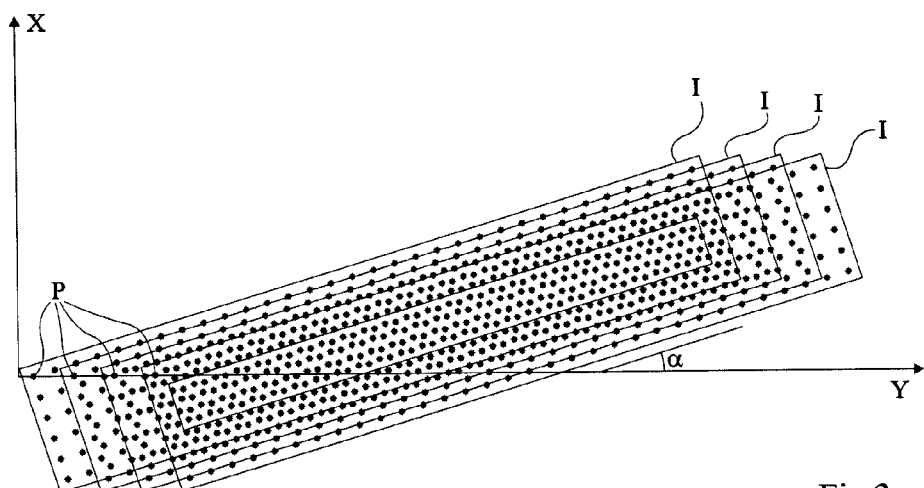
FIG. 3 illustrates the operation of the circuit of FIG. 2.

FIG. 3 is a simplified top view illustrating four respective images I taken by the array of sensors and the respective positions of object points in these images. The displacement of the object point in direction X results in that, once the images have been superposed, an object point is duplicated four times with an offset position along directions X and Y. It should be noted that this duplication does not require increasing the number of cameras in direction X.

An increase in the image resolution is obtained by superimposing the successive images taken by the sensor resulting from the displacement of the object. The image processing by a so-called super-resolution process is usual per se. The position of the images with respect to one another is, according the present invention, fixed in direction (Y) perpendicular to the displacement. Further, in the other direction (X), this position is linked to angle $\alpha$ (fixed and common to all sensors) and to the translational step between two images. In a step-by-step or continuous displacement, this translation step depends on the number of images selected for the super-resolution. The progression speed of the conveyor and the image photography frequency are selected to respect this translational step.

The pixel density in a super-resolution image depends, among others, on the number of images and on rotation angle $\alpha$ of the cameras.

Further, angle $\alpha$ conditions the homogeneity of the sampling of the objects in the images. This homogeneity may be determined based on usual image processing methods. Reference may for example be made to publication "Constrained CVT meshes and a comparison of triangular mesh generators" by Hoa Nguyen, John Burkardt, Max Gunzburger, Lili Ju, Yuki Saka, published in 2008 in Computational Geometry: Theory and Applications, Elsevier B. V. (http://www.sciencedirect.com/science?_ob=ArticleURL&_udi=B6TYS-4SCKRTM-1&_user=10&_coverDate=01%2F31%2F2009&_rdoc=1&_fmt=high&_orig=search&_sort=d&_docanchor=&view=c&_searchStrId=1379367209&_rerunOrigin=google&_acct=C000050221&_version=1&_urlVersion=0&_userid=10&md5=b799274058738c6fb4d1b52dfdd44ee7), which describes different image homogeneity determination methods, for example, the "regularity measure" (page 8).

The present inventor has observed that an angle $\alpha$ ranging between 3 and 20 degrees provides acceptable results in the desired application.

An advantage of the provided solution is that modifying angle $\alpha$ changes the translational parameter (the step between two images), and thus the resolution in both directions. As a variation, a same angle $\alpha$ satisfactory for several numbers of images, is determined in advance. The resolution can then be simply changed by modifying the step (and thus the number of images).

As a specific embodiment, a resolution for an object point approximately having a diameter of some ten micrometers (for example, 13 micrometers) by means of a 3-megapixel sensor having a nominal resolution of 52 micrometers may be obtained. With six images, a resolution equivalent to an 18-megapixel sensor having an acceptable resolution for an object of 21 micrometers is obtained.

It could have been devised to rotate the objects to be examined on the conveyor and to keep optical cameras having their pixels all aligned along a direction perpendicular to the conveying direction as in the usual solution. However, such a solution would not enable a functional super-resolution processing with a single line of cameras.

An advantage of the above-described embodiments of the present invention according to its first aspect is that they enable to decrease the number of cameras in an operation in super-resolution, which is thus less expensive. Further, the motorization of the photographic system is spared and the depth of focus is improved.

A second aspect of the present invention will be described hereafter. This aspect aims at the acquisition of three-dimensional images.

For an application to three-dimensional images, it is usual to use several cameras to take a cloud of points and, to match the images of the different cameras, to project a determined pattern on the scene. An example of a three-dimensional image processing technique is described in U.S. Pat. No. 6,545,512.

A so-called "phase-shift" technique, which comprises projecting sinusoidal patterns on the scene to be examined, is preferentially used. The interpretation of these patterns in the images is used to deduce the altitudes of the different object points of the scene.

To obtain a three-dimensional image, several cameras must observe the same portion of the scene. A problem then is that the light projected by a single registration projector risks creating shadow areas due to the very presence of the cameras in the field of the projector.

To solve this problem, it could be devised to use two projectors to light the scene according to different angles. However, the problem of overlapping areas where the projected fringes form an angle is posed. A possible solution would be to successively light the different projectors. However, this would generate an image processing time loss (time multiplied by the number of successive lightings). Another problem is that this would need projectors of high resolution, and thus expensive and currently unavailable.

According to this aspect of the present invention, a specific pattern of projected images enabling to easily solve the issue of overlapping areas between projectors is selected.

Figure 4:
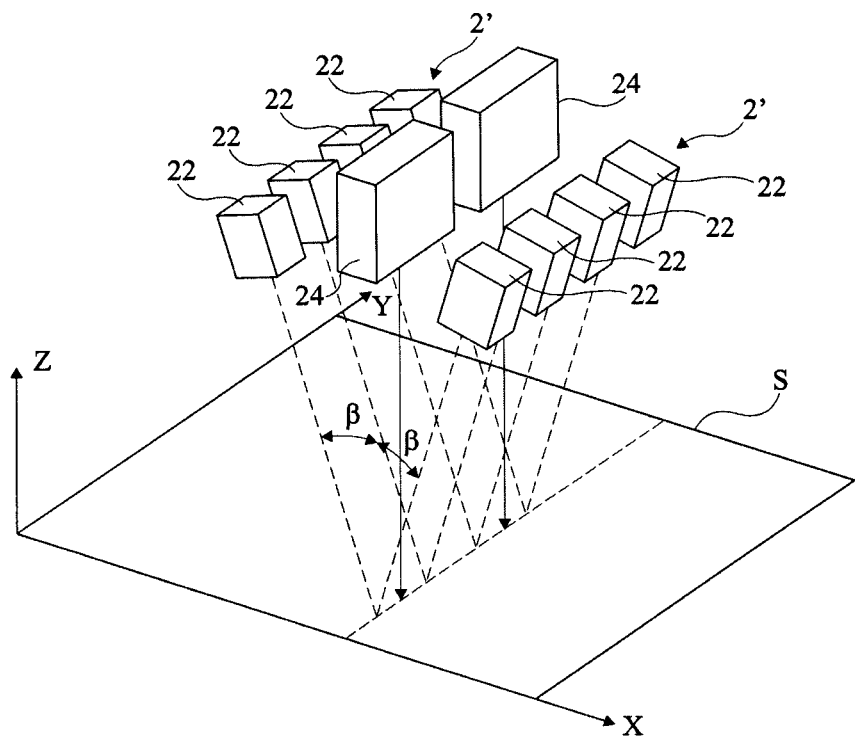
FIG. 4 is a simplified perspective view of an embodiment according to the second aspect of the present invention.

FIG. 4 is a simplified perspective view of the respective positions of cameras and of projectors according to an embodiment of the present invention. In this example, two projectors 24 of images in the scene and two groups 2' of four cameras 22 aligned along two parallel straight lines in direction Y are provided. The two groups 2' are placed on either side of projectors 24, also aligned along a line parallel to direction Y. The cameras are positioned so that their respective viewing points are aligned along direction Y and are paired up, a camera of each group aiming at the same point as the camera of the other group to which it is symmetrical with respect to axis Y. This amounts to inclining all cameras by an angle β with respect to vertical direction Z. Angle β may be identical (with different signs) for all cameras 22.

Two projectors 24 are arranged to project in the scene (in the photographed area) a determined pattern which will be described hereafter and which is recognized by the processing system. Knowing the patterns, the parameters of the projectors and the parameters of the cameras, the altitude in the scene can then be obtained.

The height of the inspected object on the conveyor is not accurate. When the object is lower than the reference height, the area located between the projectors is illuminated by the two projectors. However, if the object is higher than the reference height, part of the object can no longer be illuminated, and it is then necessary to introduce a preventive overlapping area to overcome this problem. In all cases, the overlapping area must be processed.

Either a coding is introduced in the projected images to protect the source (for example, in wavelength), or the pattern projected in the overlapping areas is such that the image processings associated with this area are independent from the projector. The present invention applies to the second solution. The constraint to be applied on the patterns is that the grey levels must be constant along the curves defined by the intersection between the image planes of the projectors and the planes containing a line interconnecting the optical centers of the two projectors.

Figure 5:
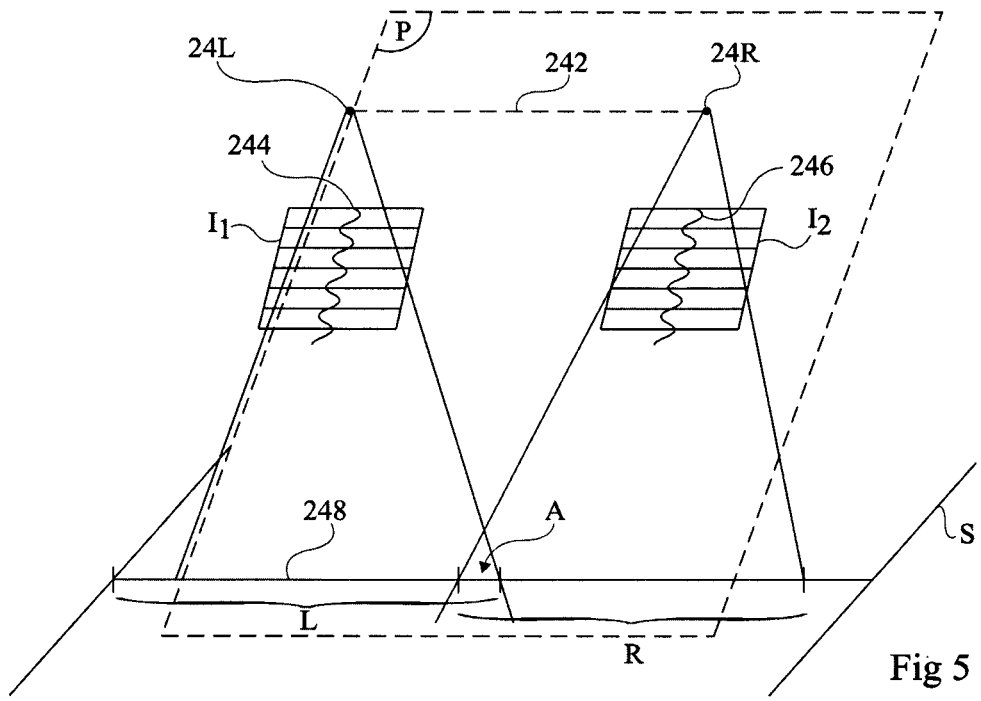
FIGS. 5 and 5A illustrate the operation of an embodiment with two projectors such as illustrated in FIG. 4.
Figure 5A:
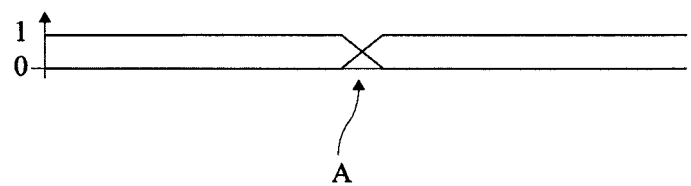

FIGS. 5 and 5A illustrate such an embodiment. FIG. 5 schematically shows an installation with two projectors. FIG. 5A schematically illustrates the intensity (luminance) of the image to be projected according to the position with respect to the overlapping area. For clarity reasons, the following explanation is not correlated to the camera system.

Two images I1 and I2 are projected by two projectors 24L and 24R on scene S corresponding to the photographed area. For example, these images are parallel lines (slots). As appears from FIG. 5, the intersection between projected images I1 and I2 and any plane P including line 242 provides parallel curves 244 and 246. Further, the projection of curves 244 and 246 on the scene provides two aligned straight lines 248 L and R. As illustrated in FIG. 5A, to respect the photometric balance of the system in overlapping area A, the image profile to be projected is adapted in this area. For example, a standardized luminance level originating from each image is adapted (decreasing on one side, increasing on the other) so that the superimposition of the two images provides a constant level on the scene.

The above embodiment is compatible with a super-resolution image processing.

A usual super-resolution processing comprising displacing the scene (or the photography set) in both directions X and Y of the plane may for example be applied.

According to a preferred example, the two described aspects are combined to apply the super-resolution process to the 3D photographic system.

Figure 6:
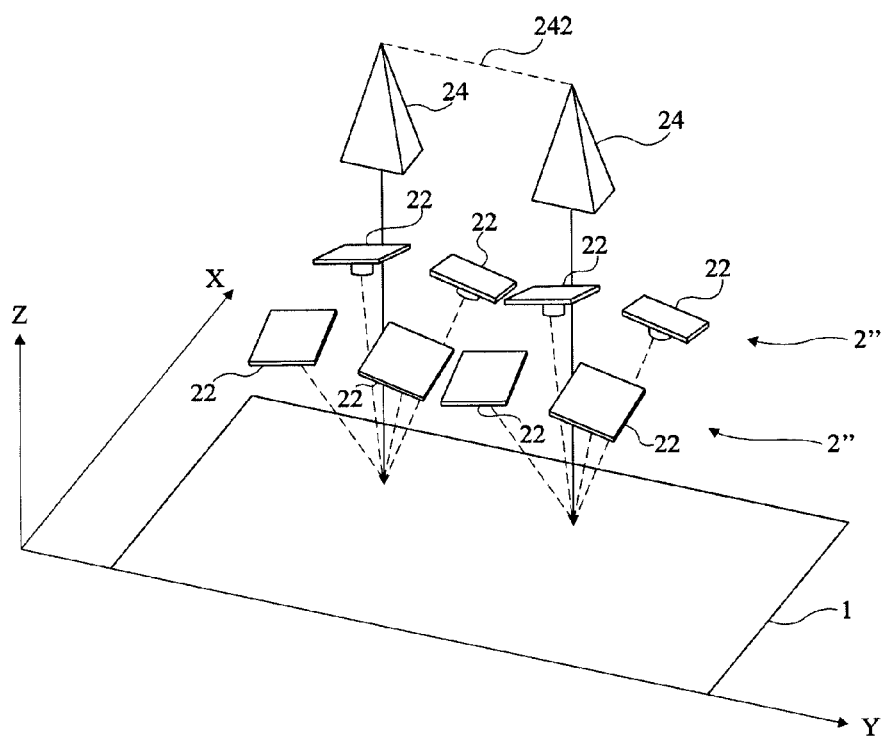
FIG. 6 is a simplified perspective view of another embodiment of an installation according to the second aspect of the present invention.

FIG. 6 is a perspective view of the photographic system of another embodiment adapted to obtaining three-dimensional (3D) images in super-resolution. For simplification, the connections to the processing system have not been shown.

Figure 7:
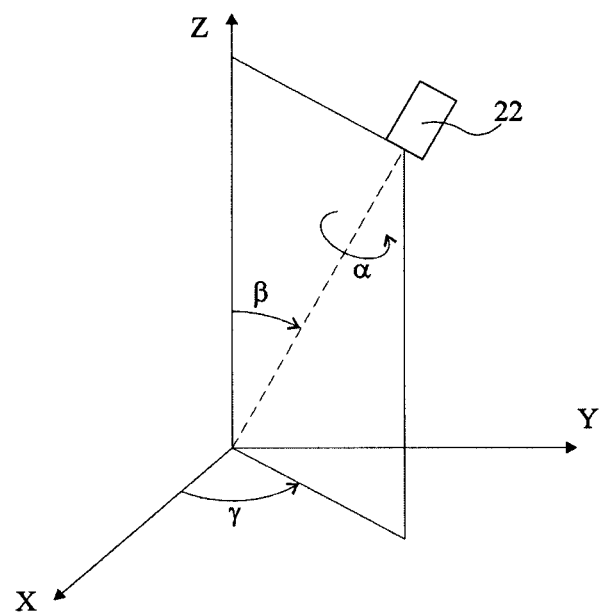
FIG. 7 is a simplified representation illustrating the angles taken into account in the installation of FIG. 6.

FIG. 7 is a geometric representation illustrating the angles involved in the installation of FIG. 6.

As compared with the embodiment of FIG. 4, cameras 22 are oriented to aim, by groups of four, at a same point. This amounts to adding a degree of liberty illustrated by FIG. 7. In addition to the inclination of angle β preferably identical in absolute value for all cameras, the cameras are rotated by an angle γ to direct their respective viewing axes, by groups of four, towards a same point.

Further, to respect to features of the first aspect, the cameras are all rotated around axis Z by an angle α.

As compared with the embodiment of FIG. 2, two series 2" of cameras 22 are arranged along two lines parallel to direction Y. In the example of FIGS. 4 and 6, each series 2', 2" comprises four cameras 22 aligned in direction Y, but this number may be different according to the width of the scene to be photographed in direction Y perpendicular to the displacement of the objects.

Angles β and γ and the viewing point are selected according to the desired accuracy along direction Z in the scene, taking the depth of focus into account.

As a specific embodiment, a system in which angle α ranges between 3 and 6 degrees may be provided, angle β ranging between 15 and 25 degrees.

Various embodiments have been described. Various alterations and modifications will occur to those skilled in the art. In particular, the selection of the position of the cameras and of the angles depends on the desired resolution and on the size of the object points to be analyzed. Other configurations than those for example described in relation with FIGS. 4 and 6 may be provided, be it in terms of number or of position of the cameras and projectors.

Further, the selection of the number of pixels per camera conditions the obtained resolution for a given conveyor speed. Further, array sensors may be used rather than square ones.

Finally, the processings to be applied to the obtained images are within the abilities of those skilled in the art based on the functional indications provided hereabove and by using usual image processing algorithms.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:

1. An apparatus for optical inspection of integrated circuits, comprising:
   a photographic system placed above a scene on a plane defined by a first direction and a second direction, the photographic system comprising a plurality of digital cameras (22) each comprising an orthogonal array of pixels, all of the digital cameras having their respective optical axes inclined by a first non-zero angle ($\beta$) with respect to a third direction (Z) perpendicular to the plane defined by the first direction and the second direction, each of the digital cameras being coplanar in another plane parallel to the plane defined by the first and second directions; and
   two projectors (24) projecting determined patterns, each of these patterns comprising a plurality of parallel lines in only one direction and being such that two straight lines respectively from the plurality of parallel lines projected by the projectors are aligned in the plane of the scene and the two straight lines are coplanar with a straight line (242) interconnecting the optical centers of the two projectors, the two straight lines forming one contiguous line,
   wherein each camera of a first subset of the plurality of digital cameras is aimed at a first point and each camera of a second subset of plurality of digital cameras is aimed at a second point,
   and wherein an image processing system is capable of applying a super-resolution processing to a succession of images provided by the photographic system.

2. The apparatus of claim 1, wherein the first angle ($\beta$) ranges between 15 and 25 degrees.

3. The apparatus of claim 1, wherein four cameras are associated with each projector and are oriented to aim at a same point on the viewing axis of this projector.

4. The apparatus of claim 1, wherein said patterns are such that two straight lines projected by each of the projectors are aligned in the plane and are coplanar with a straight line (242) interconnecting the optical centers of the two projectors.

5. The apparatus of claim 1, further comprising a conveyor of the objects to be analyzed in a first direction (X) of said plane, the photographic system (2) being placed above an area of the conveyor and in a fixed position with respect thereto and said cameras being distributed in two sets (2) of cameras aligned in a second direction (Y, Y') different from the first one, the cameras being all oriented so that one of the orthogonal directions of their pixel array forms a second angle ($\alpha$) with the first direction.

6. The apparatus of claim 5, wherein the second direction is perpendicular to the first one.

7. The apparatus of claim 5, wherein the pixels of the cameras are aligned with the second direction.

8. The apparatus of claim 5, wherein the second angle (a) ranges between 3 and 20 degrees.

* * * * *